United States Patent
Furihata et al.

(10) Patent No.: US 11,079,334 B2
(45) Date of Patent: Aug. 3, 2021

(54) FOOD INSPECTION APPARATUS, METHOD OF INSPECTING FOOD, AND METHOD OF LEARNING IN IDENTIFICATION UNIT OF FOOD INSPECTION APPARATUS

(71) Applicants: KEWPIE CORPORATION, Tokyo (JP); BRAINPAD INC., Tokyo (JP)

(72) Inventors: Kotaro Furihata, Chofu (JP); Takeshi Ogino, Chofu (JP); Kenji Suzuki, Chofu (JP); Hiromu Suzuki, Chofu (JP); Taketoshi Yamamoto, Chofu (JP); Mitsuhisa Ota, Minato (JP); Yoshimitsu Imazu, Minato (JP); Alejandro Javier Gonzalez Tineo, Tokyo (JP); Yuta Yoshida, Tokyo (JP); Yohei Sugawara, Tokyo (JP)

(73) Assignees: KEWPIE CORPORATION, Tokyo (JP); BRAINPAD INC., Tokyo (JP)

( * ) Notice: Subject to any disclaimer, the term of this patent is extended or adjusted under 35 U.S.C. 154(b) by 182 days.

(21) Appl. No.: 16/325,365

(22) PCT Filed: Aug. 22, 2017

(86) PCT No.: PCT/JP2017/029996
§ 371 (c)(1),
(2) Date: Feb. 28, 2019

(87) PCT Pub. No.: WO2018/038123
PCT Pub. Date: Mar. 1, 2018

(65) Prior Publication Data
US 2020/0386690 A1    Dec. 10, 2020

(30) Foreign Application Priority Data

Aug. 22, 2016 (JP) .............................. JP2016-162112

(51) Int. Cl.
G06K 9/00 (2006.01)
G01N 21/94 (2006.01)
G06T 7/00 (2017.01)

(52) U.S. Cl.
CPC .......... *G01N 21/94* (2013.01); *G06T 7/0004* (2013.01); *G06T 2207/30128* (2013.01)

(58) Field of Classification Search
CPC . G06T 2207/30128; G06T 2207/20081; G06T 2207/20084; G06T 2207/30108;
(Continued)

(56) References Cited

U.S. PATENT DOCUMENTS

2005/0142579 A1* 6/2005 Sugiyama ............ G01N 21/274
                                                             435/6.19
2008/0079747 A1* 4/2008 Saida ................... C12Q 1/6837
                                                             345/589
(Continued)

FOREIGN PATENT DOCUMENTS

JP        03242773 A      10/1991
JP        H06281592    *  10/1994  ............. G01N 21/89
(Continued)

OTHER PUBLICATIONS

Notice of Reasons for Refusal issued by the Japanese Patent Office in corresponding Japanese Patent Application No. 2018-529319, dated Jul. 9, 2018.
(Continued)

*Primary Examiner* — Amara Abdi
(74) *Attorney, Agent, or Firm* — Arent Fox LLP

(57) ABSTRACT

A food inspection apparatus includes: a conveyance unit; a light irradiation unit; an unit capturing an image of an inspection object A; a wavelength emphasis emphasizing a foreign substance specific wavelength characteristic of a foreign substance F from light having a wavelength of 300
(Continued)

nm to 1100 nm by using a first and/or second optical filter or a wavelength-specific light source; and an identification processing device identifying the foreign substance and including: a lightening unit normalizing the captured image with 256 or less of gradations into lightened data; and an identification unit having been provided with deep-learning of an identification processing of the foreign substance specific wavelength from the lightened data and identifying the foreign substance or a good item S in line from the lightened data obtained through capturing the image during conveyance of the inspection object.

7 Claims, 2 Drawing Sheets

(58) Field of Classification Search
CPC ....... G06T 7/0002; G06T 7/0004; G06T 7/00; G06T 7/0008; G06T 7/90; G01N 21/3581; G01N 21/94; G01N 21/31; G01N 2223/618; G01N 2223/643; G01N 33/02; G01N 33/12; G01N 15/1434; G01N 2021/845; G06K 9/00147; G06K 9/0063; G06K 2209/17; H04N 5/332
See application file for complete search history.

(56) References Cited

U.S. PATENT DOCUMENTS

| | | | |
|---|---|---|---|
| 2009/0080706 A1* | 3/2009 | Tao | G06T 7/0004 382/110 |
| 2009/0309960 A1* | 12/2009 | Park | A22C 21/00 348/61 |
| 2016/0091707 A1* | 3/2016 | Okuno | A61B 90/20 348/79 |

FOREIGN PATENT DOCUMENTS

| | | | |
|---|---|---|---|
| JP | H06281592 A | 10/1994 | |
| JP | 10300689 A | 11/1998 | |
| JP | 2001-099783 A | 4/2001 | |
| JP | 2004-301690 A | 10/2004 | |
| JP | 2005-201636 A | 7/2005 | |
| JP | 2009-115613 A | 5/2009 | |
| JP | 2012-189390 A | 10/2012 | |
| JP | 2015-197361 A | 11/2015 | |
| JP | 2016045861 A | 4/2016 | |
| JP | 2016091359 * | 5/2016 | ............ G01N 21/88 |
| JP | 2016091359 A | 5/2016 | |
| JP | 2016110290 A | 6/2016 | |
| JP | 2016-142601 A | 8/2016 | |
| WO | WO 2012/153695 A1 | 11/2012 | |

OTHER PUBLICATIONS

Internationai Search Report issued in corresponding PCT Application No. PCT/JP2017/029996 dated Nov. 7, 2017.
Sa, I, et al. "DeepFruits: A Fruit Detection System Using Deep Neural Networks", Sensors, 16, 1222, Aug. 3, 2016.
Sakai, T, et al., "Deep Learning-based Image Recognition Applications", NTT DOCOMO Technical Journal, vol. 18, No. 1, pp. 36-43, Jul. 2016.
Notice of Reasons for Refusal issued by the Japanese Patent Office in corresponding Japanese Patent Application No. 2019-109491, dated Mar. 24, 2020.
Japanese Office Action issued in corresponding Japanese Application No. JP2019-109491 dated Sep. 1, 2020.

* cited by examiner

[FIG. 1]
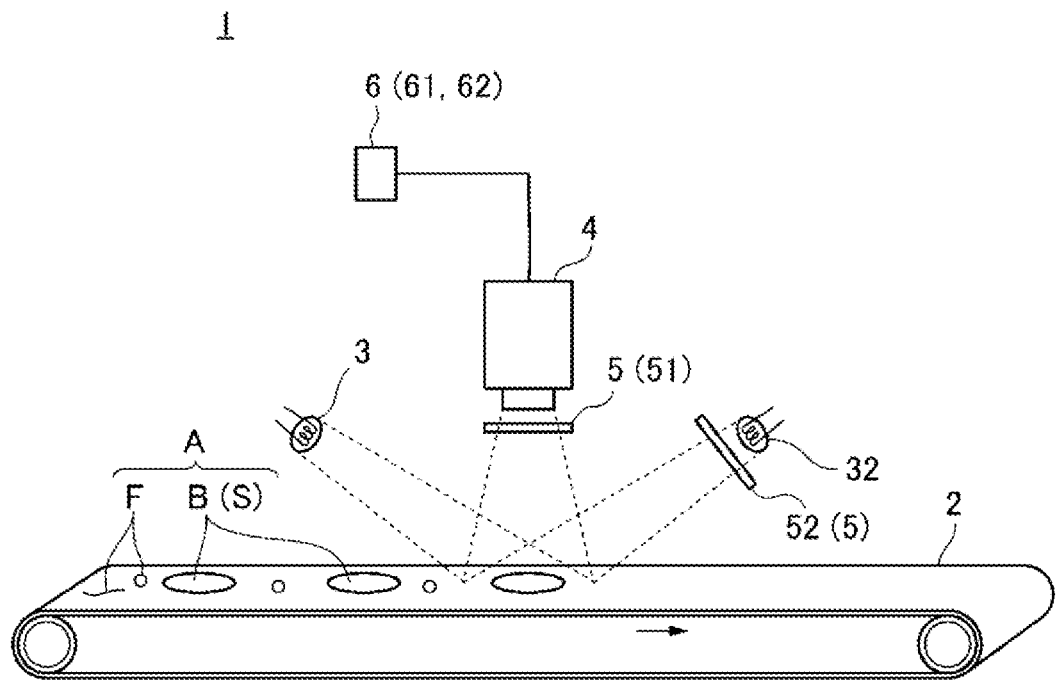
[FIG. 2]
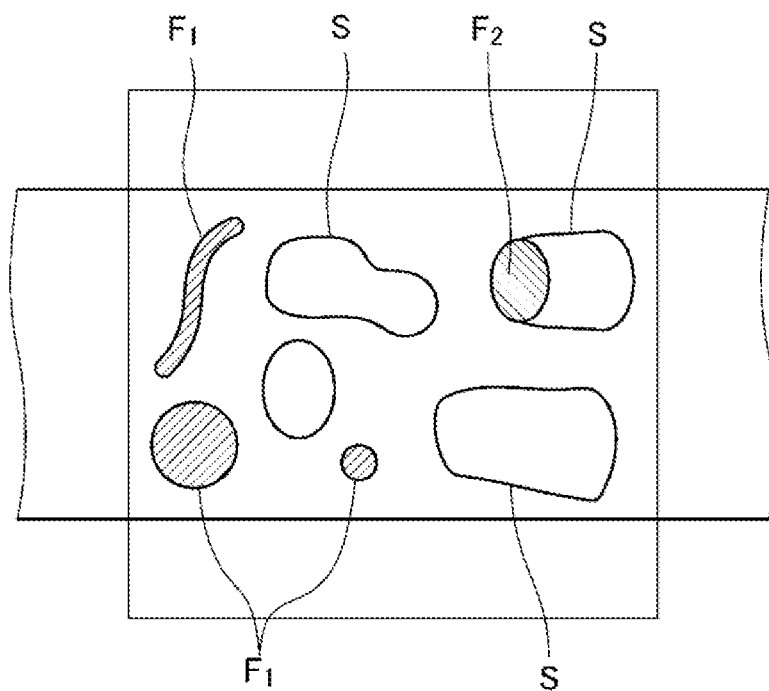

[FIG. 3]
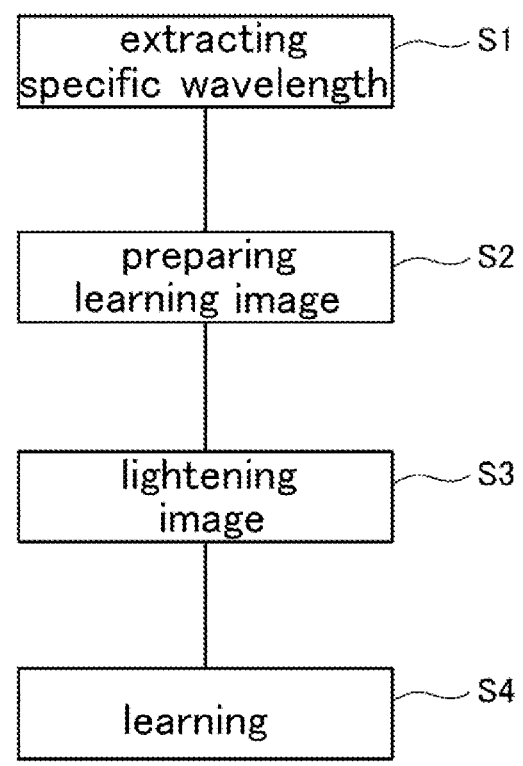

FOOD INSPECTION APPARATUS, METHOD OF INSPECTING FOOD, AND METHOD OF LEARNING IN IDENTIFICATION UNIT OF FOOD INSPECTION APPARATUS

CROSS-REFERENCE TO RELATED APPLICATIONS

This application is a National Stage Entry of International Patent Application No. PCT/JP2017/029996, filed Aug. 22, 2017, which claims priority to Japanese Patent Application No. 2016-162112, filed Aug. 22, 2016. The disclosures of the priority applications are incorporated in their entirety herein by reference.

TECHNICAL FIELD

The present invention relates to a food inspection apparatus, a method of inspecting a food, and a method of learning in an identification unit of a food inspection apparatus.

BACKGROUND ART

Description of Background Art

Conventionally, with regard to a food inspection apparatus that detects a foreign substance mixed in an inspection object such as food, various kinds of technologies such as metal detection and X-ray inspection have been proposed. In recent years, it has also been proposed to detect a foreign substance by image processing of a captured image (Patent Literatures 1 and 2).

Description of Patent Literature 1

Patent Literature 1 (see claim 1 thereof) discloses a method of detecting at least either a foreign substance or an impurity mixed in a food, including the steps of: measuring absorption spectrums of visible light and near infrared light obtained by irradiating the food and at least either the foreign substance or the impurity mixed in the food with light; performing a secondary differential processing on the absorption spectrums; selecting a wavelength range showing secondary differential spectrums different between the food and at least either the foreign substance or the impurity; acquiring a spectral image obtainable by light in the wavelength range with respect to the food by an imaging unit; and detecting at least either the foreign substance or the impurity mixed in the food by performing a second differential processing on the absorption spectrum in the wavelength range and creating a secondary differential spectral image.

Description of Patent Literature 2

Patent Literature 2 (see claim 1 thereof) discloses a method of judging a rotten portion, including the steps of: acquiring spectral images of a rotten portion sample and a fresh portion sample of decayable substances such as food; creating a calibration formula for judging whether or not each sample is a rotten portion by statistical methods using a difference in absorbance spectrum; and judging whether or not an unknown sample is a rotten portion by applying the spectral image thereof to the calibration formula.

Required Technology-1

However, in the method of Patent Literature 1, it takes time to acquire the spectral image obtainable by light in the specific wavelength range, and a processing unit of a detection apparatus duly needs a processing capacity in order to create the secondary differential spectral image from the spectral image. In addition, in the method of Patent Literature 2, detection accuracy in a processing unit of a detection apparatus is lowered, since an inspection object is divided into a plurality of regions to average a plurality of spectral images and then the spectral image of the unknown sample is applied to the calibration formula.

Required Technology-2

Therefore, in order to perform these detection or determination methods in line while keeping the detection accuracy during conveyance of the inspection object, it is necessary to set the processing unit to have a very high processing capacity or to set a conveyance speed of the inspection object as quite slow. In fact, however, it is impossible.

CITATION LIST

Patent Literature

[Patent Literature 1] Japanese Unexamined Patent Application Publication No. 2004-301690
[Patent Literature 2] Japanese Unexamined Patent Application Publication No. 2005-201636

SUMMARY OF INVENTION

Technical Problem

Problems of Background Art

The present invention has been made in view of the above circumstances, and it is therefore an object of the present invention to provide a food inspection apparatus, a method of inspecting a food, and a method of learning in an identification unit of a food inspection apparatus, which are capable of detecting a foreign substance mixed at high speed.

Solution to Problem

<First Aspect>
In order to achieve the above objective, the present invention is grasped according to the following aspects.
(1) A food inspection apparatus includes: a conveyance unit conveying a food as an inspection object to be confirmed that no foreign substance is mixed; a light irradiation unit irradiating the inspection object with light; an imaging unit capturing an image of the inspection object; a wavelength emphasis unit emphasizing a characteristic wavelength reflected by at least one of the food and the foreign substance; and an identification processing device identifying at least one of the food and the foreign substance, wherein the wavelength emphasis unit emphasizes at least one of a foreign substance specific wavelength characteristic of the foreign substance and a good item specific wavelength characteristic of a good item of the food from light having a wavelength in a range of 300 nm to 1100 nm by using a first optical filter attached to the light irradiation unit or the imaging unit and/or a second optical filter attached to an auxiliary light unit or a wavelength-specific light source, wherein the identification processing device comprises: a lightening unit normalizing the image captured by the imaging unit with 256 or less of gradations upon light intensity to be made into lightened data; and an identification unit having been in advance provided with deep-learning of an identification processing of the foreign substance specific wavelength from the lightened data by using the lightened data of plural image sheets, and wherein the identification unit identifies the foreign substance or the good item in line from the lightened data obtained through capturing the image during conveyance of the food by the conveyance unit.

<Second Aspect>

(2) In the above (1), the wavelength emphasis unit may emphasize at least one foreign substance specific wavelength and at least one good item specific wavelength, and the identification unit may identify the good item in line from the lightened data obtained through capturing the image during conveyance of the food by the conveyance unit.

<Third Aspect>

(3) In the above (2), the wavelength emphasis unit may emphasize two wavelengths of a first foreign substance specific wavelength and a second foreign substance specific wavelength as the foreign substance specific wavelength, and the identification unit may process the image captured by the imaging unit as a pseudo RGB image.

<Fourth Aspect>

(4) A method of learning in an identification unit of a food inspection apparatus, includes: a step of extracting, from a training image obtained by capturing an image of a food to be confirmed that no foreign substance is mixed, a characteristic wavelength reflected by the foreign substance as a foreign substance specific wavelength and a characteristic wavelength reflected by a good item of the food as a good item specific wavelength; a step of preparing a plurality of pseudo RGB training images at least including the foreign substance specific wavelength and the good item specific wavelength; a step of normalizing the pseudo RGB training images with 256 or less of gradations upon light intensity and lightening the images to be made into lightened learning data; and a step of providing the identification unit with deep-learning of an identification processing of the foreign substance specific wavelength or the good item specific wavelength from the lightened learning data.

<Fifth Aspect>

(5) A food inspection apparatus includes an identification unit provided with learning by a method of learning in an identification unit according to the above (4).

<Sixth Aspect>

(6) A method of inspecting a food confirms that no foreign substance is mixed in the food as an inspection object by using a food inspection apparatus according to any one of the above (1) to (3) and (5).

Advantageous Effects of Invention

According to the present invention, it is possible to provide a food inspection apparatus, a method of inspecting a food, and a method of learning in an identification unit of a food inspection apparatus, which are capable of detecting a foreign substance mixed at high speed.

BRIEF DESCRIPTION OF DRAWINGS

FIG. 1 is a schematic view showing a food inspection apparatus according to an embodiment of the present invention;

FIG. 2 is a schematic view showing an identification state of an inspection object; and FIG. 3 is a learning flow diagram of an identification unit.

DESCRIPTION OF EMBODIMENTS

Description of Embodiments—1

Hereinafter, embodiments to carry out the present invention are described in detail with reference to the accompanying drawings. Throughout the description of embodiments, the same reference signs are assigned to the same elements.

Description of Embodiments—2

First, with reference to FIG. 1, a food inspection apparatus 1 identifying a foreign substance Fn in line from a food B (an inspection object A) to be confirmed that no foreign substance Fn is mixed. FIG. 1 is a schematic view showing a food inspection apparatus according to an embodiment of the present invention. FIG. 2 is a schematic view showing the identification state of the inspection object.

<Overall Configuration of Food Inspection Apparatus—1>

The food inspection apparatus 1 shown in FIG. 1 includes a conveyance unit 2, a light irradiation unit 3, an imaging unit 4, a wavelength emphasis unit 5, and an identification processing device 6. The inspection object A to be inspected by the food inspection apparatus 1 is a food B such as not only a vegetable and a fruit before processing but also a processed product and a cooked product after processing. Examples of the foreign substance Fn that may be mixed in the food B include the followings. When only a fruit is regarded as a good item S, branches/calyx, hair, insects, metal, stone and the like may be included as an example of the foreign substance Fn. When the food B in a non-defective state is regarded as a good item S, a defective item having a wounded portion, a chipped portion, a spoiled portion, a burned portion or the like may also be included as an example of the foreign substance Fn. Further, a food different from the food B in a certain kind may also be included as an example of the foreign substance Fn. In addition, these may be combined to be the good item S or the foreign substance Fn, respectively.

<Configuration of Conveyance Unit—1>

The conveyance unit 2 conveys the inspection object A from an upstream step through an inspection step at an inspection section C to a downstream step and is configured by a belt conveyor or the like. The conveyance unit 2 conveys the inspection object A at a conveying speed of about 2 m/min to 20 m/min.

<Configuration of Inspection Section—1>

The inspection section C includes a light irradiation unit 3, an imaging unit 4, a wavelength emphasis unit 5 and an identification processing device 6, which are disposed above the conveyance unit 2. The inspection section C identifies the foreign substance Fn in line from the food B during conveyance to be confirmed that no foreign substance Fn is mixed.

<Configuration 1 of Light Irradiation Unit—1>

The light irradiation unit 3 irradiates light with a wavelength of, for example, 300 nm to 1100 nm to the inspection object A, and a halogen lamp or the like may be employed. In a case of a halogen lamp, it is possible to irradiate light from a near ultraviolet region to a visible light region and a near infrared region. In the present embodiment, the light irradiation unit 3 may also include an auxiliary light unit 32 attached with a second optical filter 52 described later.

<Configuration of Imaging Unit—1>

The imaging unit 4 captures an image of the inspection target A during conveyance, and is configured by a CCD camera, a hyper-spectral camera or the like. A first optical filter 51 described later is attached to the imaging unit 4. It should be noted that the first optical filter 51 may also be attached to the above-described light irradiation unit 3 instead of the imaging unit 4. The resolution is preferably set in a range capable of capturing an image at an average pixel length of the food B of 10 to 100 pixels, most preferably 20 to 40 pixels. When the average pixel length of the food B is smaller than 10 pixels, sufficient feature detection cannot be performed afterward, and when it exceeds 100 pixels, sufficient processing capacity as food inspection cannot be obtained. Here, the average pixel length of the food B corresponds to an average value in a set of ten images to be obtained by counting the maximum pixel number in either longitudinal or lateral direction when an image of the food B to be inspected is captured.

<Configuration of Wavelength Emphasis Unit—1>

The wavelength emphasis unit 5 emphasizes a characteristic wavelength Wn reflected by at least one of the good item S of the food B and the foreign substance Fn in the inspection object A. The wavelength emphasis unit 5 emphasizes, by using, for example, the first optical filter 51 attached to the light irradiation unit 3 or the imaging unit 4, at least one foreign substance specific wavelength (a first foreign substance specific wavelength) Wf1 characteristic of the foreign substance F1 or at least one good item specific wavelength Ws reflected by and characteristic of the good item S of the food B. In the present embodiment, a second foreign substance specific wavelength Wf2 characteristic of a foreign substance F2 other than the foreign substance F1 is also simultaneously emphasized by using the second optical filter 52.

<Configuration of Wavelength Emphasis Unit—2>

As the first optical filter 51 and the second optical filter 52, a long wavelength cut filter, a short wavelength cut filter, a band pass filter or the like may be employed. When the imaging unit 4 is a CCD camera, a CCD cell voltage external controller for externally controlling a well voltage and/or a substrate voltage of the CCD cell of the CCD camera may be employed as the first optical filter 51 and the second optical filter 52. With the CCD cell voltage external controller, the well voltage and/or the substrate voltage are controlled without changing a surface processing of a dichroic prism while using a CCD camera in a commonly available three CCD type, thereby it is possible to change response characteristics of entering photons (an energy amount varies depending on wavelength) receivable in an image element into an electric charge packet. Consequently, it is possible to emphasize at least one foreign substance specific wavelength Wf characteristic of the foreign substance F or at least one good item specific wavelength Ws reflected by and characteristic of the good item S of the food B.

<Configuration of Wavelength Emphasis Unit—3>

Furthermore, the wavelength emphasis unit 5 can emphasize not only the first foreign substance specific wavelength Wf1 and the second foreign substance specific wavelength Wf2 but also the good item specific wavelength Ws reflected by and characteristic of the good item S of the food B. It is to be noted that the first optical filter 51 and the second optical filter 52 may be configured to emphasize specific wavelengths as reversed, respectively.

<Configuration of Wavelength Emphasis Unit—4>

The first foreign substance specific wavelength Wf1, the second foreign substance specific wavelength Wf2 and the good item specific wavelength Ws have to be in advance extracted from an image D0 obtained by capturing the inspection object A.

<Configuration of Identification Processing Device—1>

The identification processing device 6 identifies the good item S of the food B or the foreign substance F1, F2 in the inspection object A. The identification processing device 6 includes a lightening unit 61 making an image D1 captured by the imaging unit 4 into lightened data D3 and an identification unit 62 identifying the first foreign substance specific wavelength Wf1, the second foreign substance specific wavelength Wf2 or the good item specific wavelength Ws from the lightened data D3.

<Configuration of Lightening Unit—1>

First, the lightening unit 61 sets the image D1 of the inspection object A captured by the imaging unit 4 during conveyance as a pseudo RGB image D2. At this time, by making correspondent the first foreign substance specific wavelength Wf1, the second foreign substance specific wavelength Wf2 and the good item specific wavelength Ws of the image D1 with any one of RGB signals in one-to-one, the image D1 is set as the pseudo RGB image D2. The pseudo RGB image D2 may be displayed on a display unit such as a monitor as necessary.

<Configuration of Lightening Unit—2>

Then, the pseudo RGB image D2 is normalized with 256 or less of gradations upon light intensity to be made into the lightened data D3. The lightest lightened data D3 is binary data.

<Configuration of Lightening Unit—3>

Here, describing a data capacity of images, when a CCD camera of 300 thousand pixels (640×480) is employed as the imaging unit 4, whereas the image D1 and the pseudo RGB image D2 captured in full color (16.77 million colors) have a data capacity of about 3.6 MB per sheet, the lightened data D has a data capacity of about 0.3 MB or less per sheet by normalizing them with 256 or less of gradations. Furthermore, by normalizing them with 16 or less of gradations, it is possible to further reduce the data capacity to 0.15 MB or less.

<Configuration of Identification Unit—1>

The identification unit 62 identifies, based on the lightened data D3, the foreign substance F1, F2 in line from the inspection object A during conveyance by the conveyance unit 2. At this time, the identification unit 62 may conversely identify the good item S in line. The identification unit 62 has been in advance provided with deep-learning of an identification processing of the foreign substance F1, the foreign substance F2 or the good item S from the inspection object A.

<Description of Method of learning in Identification Unit—1>

A method of learning in the identification unit 62 of the identification processing device 6 is described. FIG. 3 is a learning flow diagram of the identification unit.

<Description of Step of Extracting Specific Wavelengths—1>

First, in a step S1 of extracting the specific wavelengths, from a training image d1 in advance obtained with the imaging unit 4 by capturing an image of a food B to be confirmed that no foreign substance F1, F2 is mixed, characteristic wavelengths reflected by the foreign substance F1 and the foreign substance F2 as the first foreign substance specific wavelength Wf1 and the second foreign substance specific wavelength Wf2, respectively, and a characteristic wavelength reflected by the good item S of the food B as the good item specific wavelength Ws. In addition, in a case of identifying only the foreign substance F1, it is sufficient to extract the first foreign substance specific wavelength Wf1 only.

<Description of Step of Preparing Training Image—1>

In a step S2 of preparing the training image, using the wavelength emphasis unit 5 emphasizing the first foreign substance specific wavelength Wf1, the second foreign substance specific wavelength Wf2 and the good item specific wavelength Ws extracted in the step S1 of extracting the specific wavelengths, the inspection object A is captured with the imaging unit 4. The pseudo RGB training images d2 including the first foreign substance specific wavelength Wf1, the second foreign substance specific wavelength Wf2 and the good item specific wavelength Ws are created from the captured training image d1 in plural sheets, for example, in 1,000 or more sheets. At this time, by making correspondent the first foreign substance specific wavelength Wf1, the second foreign substance specific wavelength Wf2 and the good item specific wavelength Ws in the training image d1 with any one of the RGB signals in one-to-one, the pseudo RGB training images d2 are obtained.

<Description of Step of Lightening Image—1>

In a step S3 of lightening the image, the pseudo RGB training images d2 in plural sheets are normalized with 256 or less of gradations upon light intensity to be made into the lightened learning data d3.

<Description of Step of Learning—1: Deep Learning>

In a step S4 of learning, the identification unit 62 is provided with deep-learning of an identification processing of the first foreign substance specific wavelength Wf1, the second foreign substance specific wavelength Wf2 and the good item specific wavelength Ws from the lightened learning data d3. Examples of deep-learning include a so-called convolution neural network, a recursive neural network and the like. From the viewpoint that, after learning, it is necessary to process the pseudo RGB image D2 upon input, the convolution neural network is preferable.

<Description of Step of Learning—2: Convolution Neural Network>

Furthermore, in the convolution neural network, reconstruction using a self-encoder or color reconstruction using luminance are desirably employed, since it is possible to perform learning using the good item S only and advance learning steps efficiently. In this case, the reconstructed image is "a predicted image concerning a case where the captured food B corresponds to the good item S as a whole". A difference by each pixel between the reconstructed image and the lightened learning data d3 is calculated, thereby it is possible to detect pixels exceeding a predetermined threshold as "a substance not being the good item".

<Description of Step of Learning—3: Reconstruction Using Self-Encoder>

The reconstruction using the self-encoder is described in detail. In the convolution neural network of the reconstruction using the self-encoder, the lightened learning data d3 is obtained by taking out a kernel image, extracting features in a neural network layer having a plurality of nodes, and being reconstructed in a decoding layer. It is possible to extract features more conceptually by repeating the above processes from taking out of the kernel image to decoding multiple times in a nesting shape. The learning of the self-encoder is performed in such a manner that an output from a final decoding layer matches as much as possible with the lightened learning data d3 as input, that is, a loss function representing the difference becomes as low as possible. As the loss function at this time, a loss function such as BCE (Binary Cross-Entropy) may be used.

<Description of Step of Learning—4: Color Reconstruction Using Luminance>

Color reconstruction using luminance is described in detail. The lightening learning data d3 is converted from an RGB space into a Lab space to be applied to the convolution neural network of the color reconstruction using the L-value (luminance). Likewise, the a-value and the b-value converted into the Lab space are classified into categories divided into a specific number of categories on the a-b space to obtain categorical representation. In the convolution neural network of the color reconstruction using the L value (luminance), the kernel image is taken out in a first convolution layer, and then features are extracted in the neural network layer having a plurality of nodes. Next, using a deconvolution layer, the number of pixels of the original image size are reproduced. By repeating the above processes multiple times in a nesting shape (2nd, 3rd, . . . , [n]th layer), it is possible to extract features more conceptually. In the [n]th layer or the last layer, features are extracted under condition that a kernel size is the number of pixels of the original image size and the number of nodes is set as the above specific number of categories. An interval (a stride) applied in convolution is larger than two in the first convolution layer, and features are extracted from a plurality of pixels for aggregation. Conversely, in a [n−1]th deconvolution layer, while an array size (a pixel size) is the same to that of the first convolution layer and the interval applied in convolution is the same to that of the first convolution layer, features are reconstructed from one array variable to pixels in plural. In the learning of the color reconstruction using luminance, the lightened learning data d3 or the L-value of the image processing data thereof is input, and the color-reconstructed a-value and the color-reconstructed b-value of are obtained from a [n−1]th convolution layer. Thereby, the learning is performed in such a manner that the loss function (BCE) representing the difference between a set of the color-reconstructed a-value and the color-reconstructed b-value and a set of the a-value and the b-value for compact learning data of the original image becomes as low as possible. In the learning of the color reconstruction using luminance, the lightened learning data d3 of the original image or the a-value and the b-value of the image processing data thereof is input in the [n]th convolutional layer, the learning is performed in such a manner that they are classified into categories divided into a specific number of categories. The [n]th convolutional layer has the number of nodes set as the above specific number of categories, and the number of nodes is preferably 100 or more to less than 1600. When the number of nodes (the number of categories) is less than 100, a change of weight cannot be fully captured on the a-b space, and when it exceeds 1,600, the effect of improving calculation efficiency by classification into categories becomes reduced. In the inspection of the color reconstruction using luminance, a difference between the categorical representation obtained from the [n]th layer by inputting the L-value for compact learning data to the first convolution layer and the categorical representation obtained from the [n]th layer by inputting the a-value and the b-value for compact learning data to the [n−1]th convolution layer is calculated. Thereby, it is possible to detect pixels exceeding a predetermined threshold with respect to the difference as "a substance not being the good item".

<Configuration of Identification Unit—2>

In this way, the identification unit 62 provided with the learning of the relation between the foreign substance F1, the foreign substance F2 and the good item S, and the first foreign substance specific wavelength Wf1, the second foreign substance specific wavelength Wf2 and the good item specific wavelength Ws identifies, as shown in FIG. 2, the foreign substance F1, the foreign substance F2 or the good item S from the inspection object A based on the lightened data D3. In FIG. 2, the foreign substance F1 shows hair, stone, etc., and the foreign substance F2 shows a rotten portion.

<Configuration of Identification Unit—3>

At this time, the identification unit 62 may perform supplementary learning of the lightened data D3 actually obtained from the inspection object A to update the learning result.

<Overall Configuration of Food Inspection Apparatus—2>

The inspection object A identified as the foreign substance F1, the foreign substance F2 or the good item S in the inspection section C is branched or separated with a branching unit or a separating unit (not shown) or the like provided downstream of the food inspection apparatus 1. And then, the inspection object A is carried out to another route. As the branching unit or the separating unit, a branch conveyor, a robot or the like may be employed. Alternatively, when the food inspection apparatus 1 identifies the foreign substance F1 and the foreign substance F2, it may be configured to notify a worker for removal by the worker.

Effects of Embodiments—1

The effects of the embodiments as described above are described. The food inspection apparatus 1 according to the embodiment includes: a conveyance unit 2 conveying a food B as an inspection object A to be confirmed that no foreign substance Fn is mixed; a light irradiation unit 3 irradiating the inspection object A with light; an imaging unit 4 capturing an image of the inspection object A; a wavelength emphasis unit 5 emphasizing a characteristic wavelength W reflected by at least one of the food B and the foreign substance Fn; and an identification processing device 6 identifying at least one of the food B and the foreign substance Fn, wherein the wavelength emphasis unit 5 emphasizes at least one of a foreign substance specific wavelength Wf characteristic of the foreign substance Fn and a good item specific wavelength Ws characteristic of a good item S of the food B from light having a wavelength in a range of 300 nm to 1100 nm by using a first optical filter 51 attached to the light irradiation unit 3 or the imaging unit 5 and/or a second optical filter 52 attached to an auxiliary light unit 32 or a wavelength-specific light source, wherein the identification processing device 6 includes: a lightening unit 61 normalizing the image D1 captured by the imaging unit 4 with 256 or less of gradations upon light intensity to be made into lightened data D3; and an identification unit 62 having been in advance provided with deep-learning of an identification processing of the foreign substance specific wavelength Wf from the lightened data D3 by using the lightened learning data d3 of plural image sheets, and wherein the identification unit 62 identifies the foreign substance Fn or the good item S in line from the lightened data D3 obtained through capturing the image during conveyance of the food B by the conveyance unit 2. As a result, it is possible to provide the food inspection apparatus in which an identification speed is increased without degrading the accuracy of identification even not using a high speed processing unit.

Effect of Embodiment—2

In the food inspection apparatus 1 according to the embodiment, the wavelength emphasis unit 5 emphasizes the good item specific wavelength Ws reflected by the good item S. As a result, it is possible to identify the foreign substance Fn from the inspection object A and to identify the good item S. Since the good item S and the foreign substance Fn can be identified from the inspection object A (the food B), the branching unit or the separating unit can be set in details for processing based on appearance frequencies of the good item S and the foreign substance Fn.

Effect of Embodiment—3

In the food inspecting apparatus 1 according to the embodiment, the wavelength emphasis unit 5 emphasizes two wavelengths of the first foreign substance specific wavelength Wf1 and the second foreign substance specific wavelength Wf2 as the foreign substance specific wavelength Wf. As a result, it is possible to make correspondent the first foreign substance specific wavelength Wf1, the second foreign substance specific wavelength Wf2 and the good item specific wavelength Ws with any one of the RGB signals in one-to-one, and thus process the image D1 captured by the imaging unit 4 as the pseudo RGB image D2.

Effect of Embodiment—4

A method of learning in an identification unit 62 of a food inspection apparatus 1 according to the embodiment, includes: a step of extracting, from a training image d1 obtained by capturing an image of a food B to be confirmed that no foreign substance Fn is mixed, a characteristic wavelength reflected by the foreign substance Fn as a foreign substance specific wavelength Wf and a characteristic wavelength reflected by a good item S of the food B as a good item specific wavelength Ws; a step of preparing a plurality of pseudo RGB training images d2 at least including the foreign substance specific wavelength Wf and the good item specific wavelength Ws; a step of normalizing the pseudo RGB training images d2 with 256 or less of gradations upon light intensity and lightening the images to be made into lightened learning data d3; and a step of providing the identification unit 62 with deep-learning of an identification processing of the foreign substance specific wavelength Wf or the good item specific wavelength Ws from the lightened learning data d3. As a result, it is possible to efficiently provide the identification unit 62 with the learning of the relation between a set of the foreign substance Fn and the good item S and a set of the foreign substance specific wavelength Wf and the good item specific wavelength Ws.

<Description of Modification—1>

A modification of the food inspection apparatus 1 is described. In the above embodiment, the wavelength emphasis unit 5 emphasizes three wavelengths in total, that is, the first foreign substance specific wavelength Wf1, the second foreign substance specific wavelength Wf2 and the good item specific wavelength Ws. However, at least one first foreign substance specific wavelength Wf1 (Wf2) and at least one good product specific wavelength Ws may also be emphasized, or only the first foreign substance specific wavelength Wf1 may also be emphasized. By at least emphasizing the first foreign substance specific wavelength Wf1, it is possible to identify the foreign substance Fn from the food B. Alternatively, only the good item specific wavelength Ws may be emphasized. The foreign substance specific wavelength Wf and the good item specific wavelength Ws may also be configured to be emphasized in four or more as a total.

<Description of Modification—2>

In the above embodiment, the wavelength emphasis unit 5 may be a wavelength-specific light source irradiating only light within a predetermined wavelength range, for example, an LED element or a semiconductor laser in place of the second optical filter 52 attached to the auxiliary light unit. In a case of an LED element, by changing material to be contained in a LED chip, it is possible to be configured to irradiate light having a desired wavelength within a range of about 200 nm to 1,000 nm.

Although the present invention has been described with reference to the embodiments, it is needless to say that the technical scope of the present invention is not limited to the scope described in the above embodiment. It is apparent to those skilled in the art that various modifications or improvements can be added to the above embodiments. It is obvious from the description of the scope of claims that a mode with such modifications or improvements can be included in the technical scope of the present invention.

REFERENCE SIGNS LIST

1 . . . food inspection apparatus
2 . . . conveyance unit
3 . . . light irradiation unit
   32 . . . auxiliary light guide
4 . . . image pickup unit
5 . . . wavelength emphasizing unit
   51 . . . first optical filter
   52 . . . second optical filter
6 . . . identification processing device
   61 . . . lightening unit
   62 . . . identification unit
A . . . inspection object
B . . . food item, S . . . good item, Fn . . . foreign substance
Wn . . . specific wavelength

The invention claimed is:

1. A food inspection apparatus comprising:
a conveyor configured to convey a food as an inspection object to be confirmed that no foreign substance is mixed;
a light source configured to irradiate the inspection object with light;
an imager configured to capture an image of the inspection object;
a wavelength emphasizer including at least one of a first optical filter attached to the light source or the imager, a second optical filter attached to an auxiliary light source, and a wavelength-specific light source, and configured to emphasize a characteristic wavelength reflected by at least one of the food and the foreign substance; and
a processor configured to identify at least one of the food and the foreign substance,
wherein the wavelength emphasizer emphasizes at least one of a foreign substance specific wavelength characteristic of the foreign substance and a good item specific wavelength characteristic of a good item of the food from light having a wavelength in a range of 300 nm to 1100 nm,
wherein the processor is further configured to:
normalize the image captured by the imager with 256 or less of gradations of light intensity to obtain lightened data; and
be provided in advance with deep-learning to identify the foreign substance specific wavelength from the lightened data through a convolutional neural network for color reconstruction based on luminance by using the lightened data of plural image sheets, and
wherein the processor identifies the foreign substance or the good item in line from the lightened data obtained through capturing the image during conveyance of the food by the conveyor.

2. The food inspection apparatus according to claim 1, wherein the wavelength emphasizer emphasizes at least one foreign substance specific wavelength and at least one good item specific wavelength, and
wherein the processor identifies the good item in line from the lightened data obtained through capturing the image during conveyance of the food by the conveyor.

3. The food inspection apparatus according to claim 2, wherein the wavelength emphasizer emphasizes two wavelengths of a first foreign substance specific wavelength and a second foreign substance specific wavelength as the foreign substance specific wavelength, and
wherein the processor processes the image captured by the imager as a pseudo RGB image.

4. A method of learning for a processor of a food inspection apparatus, comprising:
extracting, from a training image obtained by capturing an image of a food to be confirmed that no foreign substance is mixed, a characteristic wavelength reflected by the foreign substance as a foreign substance specific wavelength and a characteristic wavelength reflected by a good item of the food as a good item specific wavelength;
preparing a plurality of pseudo RGB training images at least including the foreign substance specific wavelength and the good item specific wavelength;
normalizing the pseudo RGB training images with 256 or less of gradations of light intensity and lightening the images to obtain lightened learning data; and
providing the processor with deep-learning to identify the foreign substance specific wavelength of the good item specific wavelength from the lightened learning data through a convolutional neural network for color reconstruction based on luminance.

5. A food inspection apparatus comprising a processor provided with learning by the method of learning according to claim 4.

6. A method of inspecting a food, confirming that no foreign substance is mixed in the food as an inspection object by using a food inspection apparatus according to claim 1.

7. A method of inspecting a food, confirming that no foreign substance is mixed in the food as an inspection object by using a food inspection apparatus according to claim 5.

* * * * *